United States Patent [19]

Nelson

[11] 4,224,452
[45] Sep. 23, 1980

[54] METHOD FOR PREPARING 4-HYDROXYMETHYL IMIDAZOLES

[75] Inventor: Gunner E. Nelson, Baton Rouge, La.

[73] Assignee: Ethyl Corporation, Richmond, Va.

[21] Appl. No.: 882,801

[22] Filed: Mar. 2, 1978

[51] Int. Cl.$^2$ ............................................ C07D 233/64
[52] U.S. Cl. ..................................... 548/342; 548/336
[58] Field of Search ......................................... 548/342

[56] References Cited

U.S. PATENT DOCUMENTS

| | | | |
|---|---|---|---|
| 3,950,333 | 4/1976 | Durant et al. | 424/250 X |
| 3,984,293 | 10/1976 | King et al. | 204/75 |
| 4,055,573 | 10/1977 | Mendelson | 548/335 |

FOREIGN PATENT DOCUMENTS 1341376 12/1973 United Kingdom.

OTHER PUBLICATIONS

Daniels et al., J. Org. Chem., 1962, vol. 27, pp. 4710-4711.
Jaques et al., J. Chem. Soc., (London), 1964, pp. 2683-2689.
Patai, The Chemistry of the Ether Linkage, pp. 22-42, N.Y., Interscience-Wiley, 1967.
Fieser et al., Organic Chemistry, 3rd ed., p. 137, N.Y., Reinhold, 1956.
Hofmann, Imidazole and Its Derivatives, Part I, pp. 16-17, N.Y., Interscience, 1953.
Noller, Chemistry of Organic Compounds, 2nd ed., W. B. Saunders Co., Phila., 1957, pp. 139-140.

*Primary Examiner*—Henry R. Jiles
*Assistant Examiner*—Richard A. Schwartz
*Attorney, Agent, or Firm*—Donald L. Johnson; John F. Sieberth; James M. Pelton

[57] ABSTRACT

A method for preparing 4-(hydroxymethyl)-imidazoles from crude solutions containing bis-imidazole ethers by hydrolyzing in dilute solution at elevated temperatures.

4 Claims, No Drawings

METHOD FOR PREPARING 4-HYDROXYMETHYL IMIDAZOLES

BACKGROUND OF THE INVENTION

This invention relates to a process for preparing various 4-(hydroxymethyl)-imidazoles, and, particularly, their hydrochlorides. These compounds are intermediates for preparing commercially important medicinal agents having histamine $H_2$-agonist activity of which the inhibition of gastric secretion is one medical indication (see Black et al, Nature, 1972, 236-385). An example of one of these end products is cimetidine, N-cyano-N'-methyl-N"-[5-methyl-4-imidazolyl-(methylthio)-ethyl]-guanidine, U.S. Pat. No. 3,950,333.

In U.S. Pat. No. 3,984,293, there is described the state of the art as background to the electrochemical reduction of 4-imidazole carboxylic acids. That invention is useful, however, it necessitates an extra chemical step prior to reduction, namely, hydrolysis of the ester intermediate to form the free carboxylic acid. Also, U.S. Pat. No. 4,055,573 teaches a method for preparing 4-(hydroxymethyl)-imidazoles and their lower alkyl ethers by electrochemical reduction in concentrated sulfuric acid in concentrated solutions using standard electrochemical cells with yields up to 80%. It should be noted that, although the imidazole alcohol is produced, an equally important product is imidazole ethyl ether. Subsequent reaction of the mixed alcoholalkyl ether with cysteamine hydrochloride produces the thioamine in about 60% yield. Further, in British Pat. No. 1,341,376 the reduction of 4-methyl-5-carbethoxyimidazole with lithium aluminum hydride, followed by addition of water, filtration and acidification with hydrochloric acid, affords 4-methyl-5-hydroxymethylimidazole hydrochloride. Although the yield is not given, it appears to amount to about 60%. Subsequent reactions produced 4-methyl-5-(2-aminoethyl)-imidazole.

In the production of 4-(hydroxymethyl)-imidazole hydrochloride, it is always an objective to minimize the production of by-products because they represent yield losses and impurities which are more preferably avoided for economic, purification and governmental regulatory reasons. However, several processes for making such 4-(hydroxymethyl)-imidazoles can produce substantial quantities of imidazole ethers. Such ethers can also be produced by heating 4-(hydroxymethyl)-imidazole compounds at temperatures from about 40 to about 60° C. for periods of time ranging from 2 to about 3 hours. Further, such compounds are not formed in as great an amount at lower temperatures. Accordingly, processes which can remove or purify the 4-(hydroxymethyl)-imidazoles of such imidazole ester compounds are useful and desirable.

THE INVENTION

In view of the foregoing, it is indeed surprising that such imidazole ether compounds can be converted to the 4-(hydroxymethyl)-imidazole hydrochlorides by reaction with water at elevated temperatures. Preferably, the present invention includes a method for preparing a 4-(hydroxymethyl)-imidazole hydrochloride which comprises reacting a compound of formula

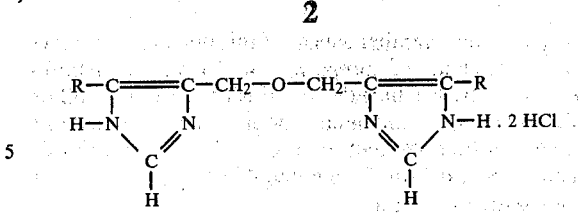

wherein R is the same alkyl group having from 1 to 4 carbon atoms with water at elevated temperature. Compounds of the above general formula are particularly referred to as bis-4-(5-alkyl)-imidazolyl methyl ethers but for convenience will be hereinafter referred to as "bis-ethers". More preferably, the method entails reacting bis-ethers in a dilute aqueous acidic solution of the desired product 4-(hydroxymethyl)-imidazole hydrochloride. In one embodiment, the 4-(hydroxymethyl)-imidazole hydrochloride is 5-methyl-4-(hydroxymethyl)-imidazole hydrochloride. Conveniently, the acid used to render the solution acidic is hydrochloric acid.

Preferably, the reaction is carried out at elevated temperatures. Thus, the temperatures must be high enough to facilitate the reaction but not so high as to seriously degrade the product 4-(hydroxymethyl)-imidazole hydrochloride. Generally, temperatures between about 100°-130° C. have been found to produce satisfactory results.

The reaction is also found to be conveniently carried out in a dilute solution. For the purposes of this invention, a dilute solution is defined as being about 10 weight percent of the crude 4-(hydroxymethyl)-imidazole hydrochloride or less. The bis-ether compound may amount initially to about 2 to about 65 weight percent of the crude 4-(hydroxymethyl)-imidazole, preferably, the bis-ether amounts to less than about 20% of the crude imidazole material in the dilute solution.

The present method can be more fully understood from the following examples:

EXAMPLE 1

Two 5 weight percent aqueous solutions of crude 4-(hydroxymethyl)-imidazole hydrochloride containing 14 weight percent of bisether at a pH of 2.5-3 are heated at 100° C. and 130° C., respectively. The product composition is analyzed with time and the results are given below:

| Time (hr) | 4-(Hydroxymethyl)-imidazole hydrochloride, % | *Bis-ether, % |
|---|---|---|
| | 100° C. | |
| 0 | 82 | 14.1 |
| 20 | 91 | 3.0 |
| 29 | 92 | 1.9 |
| 44 | 95 | 1.7 |
| | 130° C. | |
| 0 | 82 | 14.1 |
| 4 | 93 | 1.6 |
| 8 | 96 | 1.4 |
| 16 | 90 | 1.3 |

*in which R from the preceding formula is methyl.

As can be clearly seen from the above example, the increase of temperature as time increases during the first 4-20 hours drastically reduces the bis-ether content of the crude 4-(hydroxymethyl)-imidazole hydrochloride material. This makes the present method eminently suitable for treating imidazole products which contain substantial amounts of bis-ether to reduce the bis-ether content. Thus, another aspect of this invention provides for a method of preparing a 4-(hydroxymethyl)-imidazole hydrochloride comprising heating a dilute aqueous solution containing about 5 weight percent of a crude 4-(hydroxymethyl)-imidazole hydrochloride which contains from 2 to about 40 weight percent of a compound of formula

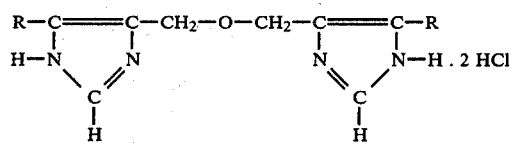

wherein R is the same alkyl group having from 1 to 4 carbon atoms at a temperature from about 100° to about 130° C. at a pH of from about 2½ to about 3.

EXAMPLES 2–9

Following the procedure of Example 1, several dilute solutions of crude 4-(hydroxymethyl)-imidazole hydrochloride were treated according to the process of this invention. The conditions and results are given in the table below:

| Example No. | Concentration of Crude 4-(hydroxymethyl)-imidazole hydroxhloride in Water (wt %) | Temp. (°C.) | Time (hrs.) | Product Composition, Dry Basis (wt %) | | |
|---|---|---|---|---|---|---|
| | | | | 4-(hydroxymethyl)-imidazole hydrochloride | Bis-ether | Methyl Imidazole Impurity |
| 2 | 5 | 100[a] | 0 | 82 | 14.1 | 0.3 |
| | | | 20 | 91 | 3.0 | 0.4 |
| | | | 29 | 92 | 1.9 | 0.6 |
| | | | 44 | 95 | 1.7 | 0.6 |
| 3 | 10 | 100 | 0 | 82 | 14.1 | 0.3 |
| | | | 20 | 89 | 4.6 | 0.6 |
| | | | 68 | 87 | 4.4 | 0.6 |
| 4 | 5 | 130[b] | 0 | 82 | 14.1 | 0.3 |
| | | | 4 | 93 | 1.6 | 0.7 |
| | | | 8 | 96 | 1.4 | 1.1 |
| | | | 16 | 90 | 1.3 | 1.4 |
| 5 | 10 | 130 | 0 | 82 | 14.1 | 0.3 |
| | | | 4 | 93 | 3.2 | 0.7 |
| 6 | 5 | 115[b] | 0 | 82 | 14.1 | 0.3 |
| | | | 7 | 91 | 1.9 | 0.6 |
| 7 | 10 | 115 | 0 | 82 | 14.1 | 0.3 |
| | | | 7 | 93 | 3.6 | 0.8 |
| 8 | 5 | 130 | 0 | — | 61.4 | 0.3 |
| | | | 4 | — | 4.7 | 0.6 |
| | | | 8 | 91 | 1.8 | 0.6 |
| 9 | 5 | 115 | 0 | — | 61.4 | 0.3 |
| | | | 20 | 96 | 1.8 | 1.0 |

[a]Open system under reflux at ambient pressure.
[b]Closed system at autogenous pressure estimated to approximate vapor pressure of water; i.e., about 25 psi at 115° C. and about 40 psi at 130° C.

Having described the invention, it is clear that numerous variations and changes will occur to one skilled in the art which nevertheless would be within the concept of the invention. Therefore, it is desired that the present invention be limited only by the lawful scope of the following claims.

What is claimed is:

1. The method of treating crude 5-loweralkyl-4-(hydroxymethyl)-imidazole hydrochloride containing a bis-(imidazolylmethyl)-ether to reduce the bis-ether content comprising heating a dilute aqueous solution containing crude 5-loweralkyl-4-(hydroxymethyl)-imidazole hydrochloride which contains from 2 to about 65 weight percent of a bis-(imidazolylmethyl)-ether of formula

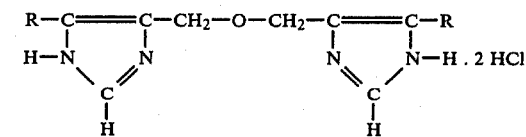

where each R is the same alkyl group having from 1 to 4 carbon atoms at an elevated temperature at a pH of from about 2.5 to about 3, using hydrochloric acid to effect said pH.

2. A method for preparing 5-loweralkyl 4-(hydroxymethyl)-imidazole hydrochloride which comprises reacting a bis-(imidazolylmethyl)-ether compound of formula

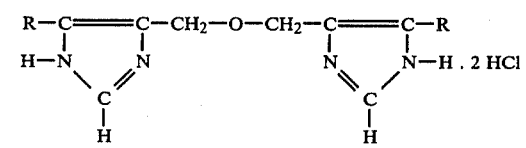

wherein R is the same alkyl group having from 1 to 4 carbon atoms with water at a pH of about 2.5 to about 3 and at an elevated temperature, using hydrochloric acid to effect said pH.

3. The method of claim 2 in which said 5-loweralkyl-4-(hydroxymethyl)-imidazole hydrochloride is 5-methyl-4-(hydroxymethyl)-imidazole hydrochloride.

4. The method of claim 2 wherein said elevated temperature is between about 100° and 130° C.

* * * * *